(12) United States Patent
     Bellini

(10) Patent No.: US 10,569,002 B2
(45) Date of Patent: Feb. 25, 2020

(54) PORTABLE MEDICAL APPARATUS FOR CARDIOPULMONARY AID TO PATIENTS

(71) Applicant: RAND S.r.l., Medolla (MO) (IT)

(72) Inventor: Corrado Bellini, Medolla (IT)

(*) Notice: Subject to any disclaimer, the term of this patent is extended or adjusted under 35 U.S.C. 154(b) by 347 days.

(21) Appl. No.: 15/490,070

(22) Filed: Apr. 18, 2017

(65) Prior Publication Data
    US 2017/0216509 A1    Aug. 3, 2017

Related U.S. Application Data

(63) Continuation-in-part of application No. 13/881,224, filed as application No. PCT/IB2011/054921 on Nov. 4, 2011, now abandoned.

(30) Foreign Application Priority Data

Nov. 5, 2010    (IT) .............................. MO2010A0311

(51) Int. Cl.
    *A61M 1/36*      (2006.01)
    *A61M 1/16*      (2006.01)

(52) U.S. Cl.
    CPC ........ *A61M 1/1698* (2013.01); *A61M 1/1629* (2014.02); *A61M 1/3626* (2013.01); *A61M 1/3666* (2013.01); *A61M 2205/3673* (2013.01); *A61M 2205/502* (2013.01); *A61M 2209/08* (2013.01); *A61M 2230/207* (2013.01); *A61M 2230/30* (2013.01); *A61M 2230/50* (2013.01)

(58) Field of Classification Search
    CPC .......................... A61M 1/3666; A61M 1/1698
    See application file for complete search history.

(56) References Cited

U.S. PATENT DOCUMENTS

| | | | | |
|---|---|---|---|---|
| 5,514,335 A | * | 5/1996 | Leonard | A61M 1/1698 210/321.6 |
| 2002/0161349 A1 | * | 10/2002 | Allers | A61M 1/369 604/500 |
| 2008/0027368 A1 | * | 1/2008 | Kollar | A61M 1/3621 604/6.14 |
| 2009/0114379 A1 | * | 5/2009 | Lim | B23P 15/26 165/151 |

\* cited by examiner

*Primary Examiner* — Kai H Weng
(74) *Attorney, Agent, or Firm* — Themis Law

(57) ABSTRACT

A portable medical apparatus for cardiopulmonary aid to patients includes a transportable machine body that integrates an heater/cooler unit and an extracorporeal circuit for circulating the blood of a patient. The extracorporeal circuit includes a line for drawing venous blood from the patient, a line for returning arterial blood to the patient, a pumping unit for pumping blood along the extracorporeal circuit, a heat exchanger for thermoregulating blood in the extracorporeal circuit, and an oxygenator unit for blood oxygenation.

13 Claims, 8 Drawing Sheets

PORTABLE MEDICAL APPARATUS FOR CARDIOPULMONARY AID TO PATIENTS

FIELD OF THE INVENTION

The invention relates to a portable medical apparatus for cardiopulmonary aid to patients, particularly for aid to patients struck by sudden and serious diseases in areas remote from health care facilities, for performing appropriate treatments for immediate care and for rescue of these patients.

BACKGROUND OF THE INVENTION

The management of cardiopulmonary bypass and temporary cardiopulmonary support systems has been long using equipment integrating a variety of medical devices, which are of similar types and also available as individually operating devices, which form as a whole an extracorporeal circuit.

These apparatus, also known as heart-lung machines, use extracorporeal circuits having a considerably low degree of integration with the apparatus.

This has the main purpose of allowing users to use a common apparatus, to be equipped with disposable devices mounted and used thereon, which have equivalent performances but are produced by different manufacturers, and allowing users to adapt a circuit to their own requirements and available spaces.

A disposable extracorporeal circuit typically comprises venous and arterial cannulas which are placed by surgery or percutaneous methods on a vascular access of relevant size, e.g. the venae cavae or the femoral vein for the venous section and the descending aorta or femoral artery for the arterial section.

These cannulas form the interface between the disposable circuit on the apparatus and the patient.

The circuit is composed of a tube that drains blood from the patient, also known as venous return, a soft container (bag) or a rigid container, a venous reservoir for collecting blood from the patient, a pump, an oxygenator with an integrated heat exchanger, an arterial filter and a number of tubes for interconnecting these elements and allowing easy filling and monitoring thereof during use.

Nevertheless, the possibility of using a variety of devices with a single apparatus limits integration of the various disposable devices and increases the likelihood of inducing errors in their use, with the risk of affecting patient's safety.

Particularly, air may enter the extracorporeal circuit from a number of points, typically from the venous cannula, or from the many connections between extracorporeal tubes interconnecting the various devices of the circuit, or due to not easily predictable intra-operative events.

Therefore, there is the need of minimizing the ingress of air into the blood circulating in the extracorporeal circuit, by removing it before it reaches the last elements of the circuit (namely the heat exchange and the oxygenator) to prevent hazardous events for the patient.

In clinical practice, both venous and arterial cannulas shall be entirely filled with the patient's blood, whereas a blood biocompatible filling solution, typically a saline or another electrolyte-rich solution is used to fill the entire extracorporeal circuit, before coupling the cannulas filled with the patient's blood to the circuit filled with such solution. The blood volume and/or biocompatible solution pumped into the circuit is known as "priming volume".

Typically, the whole extracorporeal circuit is "washed" with $CO_2$ before being filled with the above mentioned solution, because this gas (i.e. carbon dioxide) both simplifies removal of air from the circuit, and dissolves more easily in the filling solution.

Then, such filling solution pushes the "washing" $CO_2$ out of the circuit and facilitates full removal thereof.

Next, once the whole circuit has been filled, and any air and micro-bubbles have been removed, blood flow is started by opening the venous cannula whereupon, as soon as blood starts to flow within the circuit, the arterial cannula is also opened.

The circuit volume should be minimized, because the filling solution dilutes the patient's blood, thereby impacting his/her hemodynamic conditions.

In an attempt to obviate the above drawbacks, circuits with smaller and smaller volumes have been developed which, in spite of the resulting reduction of air trapping devices, were found to achieve the same effectiveness, by using more or less automatic systems for quickly blocking and removing air from the circuit, possibly without requiring any action by an operator for this delicate and critical operation, which is required to ensure safety against accidental ingress of air into the circuit and hence into the patient, and thus avoid any possible gas embolism.

This necessarily involved an evolution of the apparatus designed to manage these mini-circuits, which should ensure a considerable degree of integration between disposable devices and hardware and software devices.

Such an apparatus is disclosed by Patent Application US2006/0122551A1, in which the entire disposable circuit is pre-assembled into some sort of cartridge, which is precision-fitted into a specially designed apparatus.

In terms of structure, this apparatus uses the prior art technique as used for closed-loop cardiopulmonary bypass, in which a soft reservoir, typically consisting of a deformable bag, collects the venous blood from a patient, a centrifugal pump draws and conveys it to an oxygenator having an integral heat exchanger.

Then, the pump thrust conveys blood from the oxygenator to an arterial filter and then, via a tube, back to the patient.

The "patient" module as disclosed in the patent comprises a series of separate elements, which are assembled together to a minimized size on a support frame that forms some sort of cartridge, adapted to be mounted to the apparatus using preset interfaces, that engage the cartridge in the priming position.

The peculiar feature of this device is that during the priming step the whole circuit is oriented along an axis that facilitates removal of air from the disposable device.

Once priming has been completed the cartridge rotates integrally with a portion of the apparatus, indicatively through 90° from the priming position and prepares for use with the patient.

Patent Application US2007/0009378A1 discloses a device for control of extracorporeal blood circulation, which comprises at least one oxygenator, a heat exchanger and a blood filter, having the inlet and outlet connections of the oxygenator/heat exchanger so incorporated that blood flow has a hydraulic section of 80 $mm^2$ or more or preferably 120 $mm^2$ or more.

The disclosed device may operate both separately and as a structural part that combines the operations of an oxygenator, a heat exchanger and a blood filter.

Patent Application US2009/0175762A1 also discloses a device for control of extracorporeal blood circulation, which comprises at least one venous reservoir, a centrifugal pump, an oxygenator, and means for interconnecting them into a structural unit that combines the operations of an oxygenator, a heat exchanger and a blood filter.

This patent discloses a device that separates air from the patient's blood, which is drained by the negative pressure created by the rotation of a centrifugal pump.

A bubble removing device is placed between the patient's blood drainage line and the centrifugal pump and is interfaced via a special sensor to a regulating unit.

The above described prior art suffers from certain drawbacks.

A first drawback is that prior art heart-lung apparatus use water-supplied/thermostated heat exchanger devices. Therefore, for proper operation they must be combined with large apparatus, such as thermostated baths or thermostated reservoirs, that are not easily transportable.

Since prior art heat exchangers rely on a source of a temperature-regulating fluid, operators must carry patients with cardiogenic shock or serious cardiopulmonary failure caused by an acute event, such as myocardial infarction or post-traumatic hypovolemia, from the place where injury occurs to the hospitals in which heart-lung machines are available and stably connected to such sources of temperature-regulating fluid.

This involves a critical time loss, before starting treatments for rescuing the patient.

A further drawback is that patient aid only generally relates to circulation, hence artificial aid in cardiac output and the associated lung function, using pumps and an oxygenator, without using, for instance, induced and/or controlled hypothermia, to keep the brain and heart functions of the patient unaltered and as effective as possible.

Another drawback is that physical parameters, such as pressure and temperature are monitored using probes and electric cables that are directly connected to the apparatus but are not ergonomically integrated thereon, which is a limit both in terms of system preparation times, as well as in system completeness and compactness.

A further drawback is that prior art systems do not include integral apparatus for monitoring hematochemical parameters, such as pH, partial pressures of $O_2$ and $CO_2$, which are critical parameters for proper therapeutic treatment and which can only be detected by combined use of special auxiliary instruments.

Yet another drawback is that prior art systems do not include integrated oxygen or pre-mixed gas bottles for ventilation of the oxygenator units used by these systems.

Therefore, the system cannot be adequately used in cases of emergency, or when patients have to be transported in critical conditions, unless combined use is made of auxiliary instruments which have a large size and are not easily transportable.

SUMMARY OF THE INVENTION

It is an object of the present invention to improve the prior art.

Another object of the invention is to provide a portable medical apparatus for cardiopulmonary aid to patients that provides aid to patients struck by sudden and serious cardiovascular diseases even outside hospital facilities, directly in the place where such diseases occurred.

Yet another object of the invention is to provide a portable medical apparatus for cardiopulmonary aid to patients, that has most of its components integrated into a single compact machine body.

In one aspect, the invention provides a portable medical apparatus for cardiopulmonary aid to patients as defined hereinafter.

Therefore, the invention provides the following advantages:

Rescuing patients struck by sudden and serious cardiovascular diseases in the place where the disease occurred, without having to carry the patient to a specially equipped hospital facility;

Considerably reducing intervention times and hence increasing survival rates in patients struck by serious diseases;

Carrying out treatments on site, which also require temperature control of patients' organic fluids, such as blood;

Considerably reducing the overall size of extracorporeal circuits and the components associated therewith and used to carry out rescue therapies;

Providing disposable components designed to be placed on the extracorporeal circuits, which can be quickly mounted with no possibility of errors by the operators;

Assembling the whole extracorporeal circuit and its components into a single compact, standalone and easily transportable rescue unit;

Providing a standalone rescue unit that can follow patients from the first aid location to an organized hospitalization facility, such as a hospital, a clinic or an outpatients' department, while maintaining uninterrupted therapy from the first aid intervention.

BRIEF DESCRIPTION OF THE DRAWINGS

Further features and advantages of the invention will be more readily apparent upon reading of the detailed description of a preferred non-limiting embodiment of a portable medical apparatus for cardiopulmonary aid to patients, which is shown by way of illustration and without limitation by the annexed drawings, in which.

DETAILED DESCRIPTION OF EMBODIMENTS OF THE INVENTION

Figure 1:
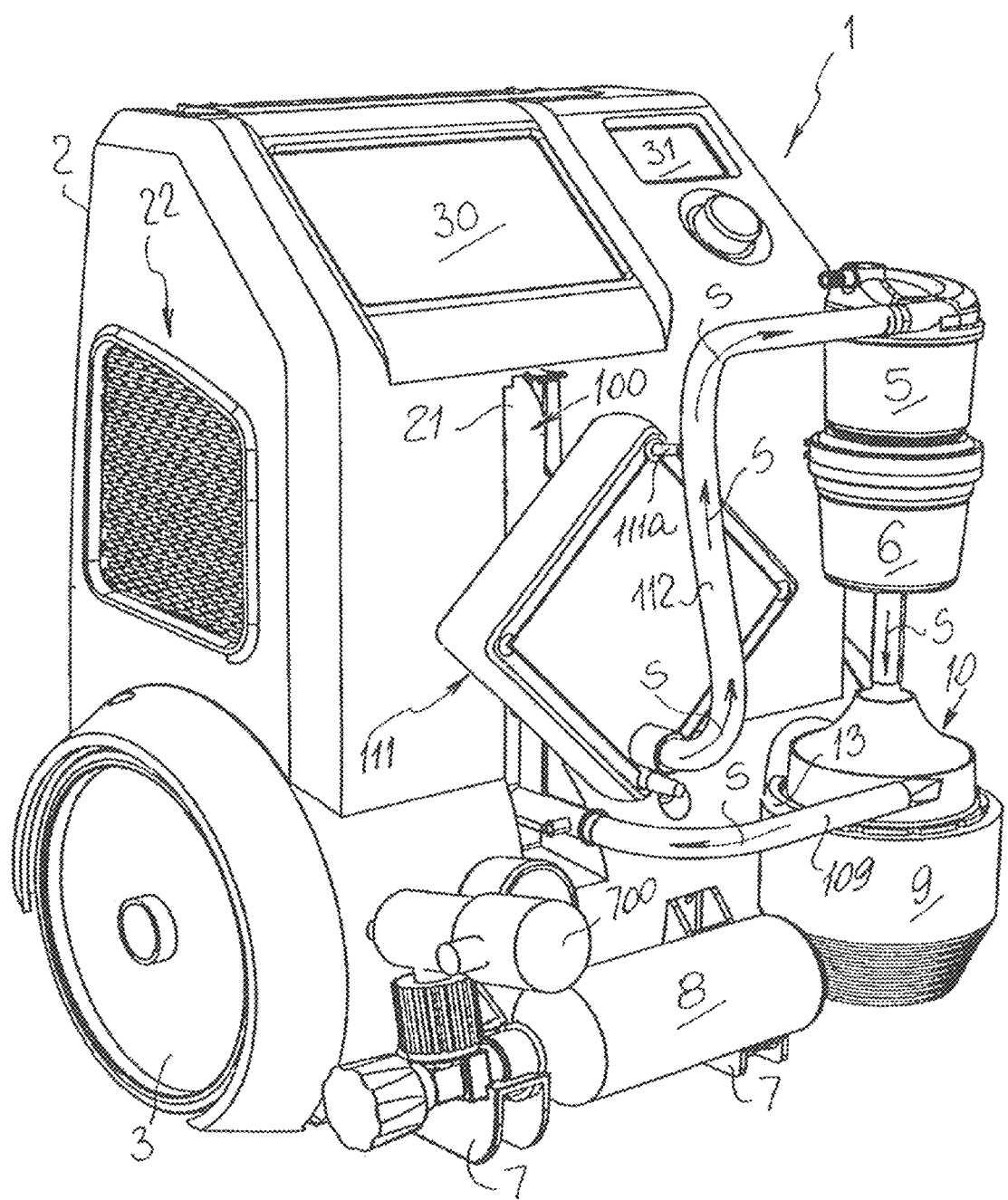
FIG. 1 is a perspective view of a portable medical apparatus for cardiopulmonary aid to patients, as taken under a first angle of view.

Referring to the figures, numeral 1 generally designates a portable medical apparatus for cardiopulmonary aid to patients, according to the invention.

The medical apparatus 1 comprises a machine body 2 which encloses, as better explained below, an extracorporeal circuit, schematically and generally referenced 500 in FIG. 4, for treating blood of a patient "P".

The machine body 2 has a pair of wheels 3 in its lower portion, making the machine body 2 movable over a floor and, in its upper portion, an extractable handle 4, for lifting and dragging it, which is slideably held in a compartment 206 formed on the back of the machine body 2.

Figure 5:
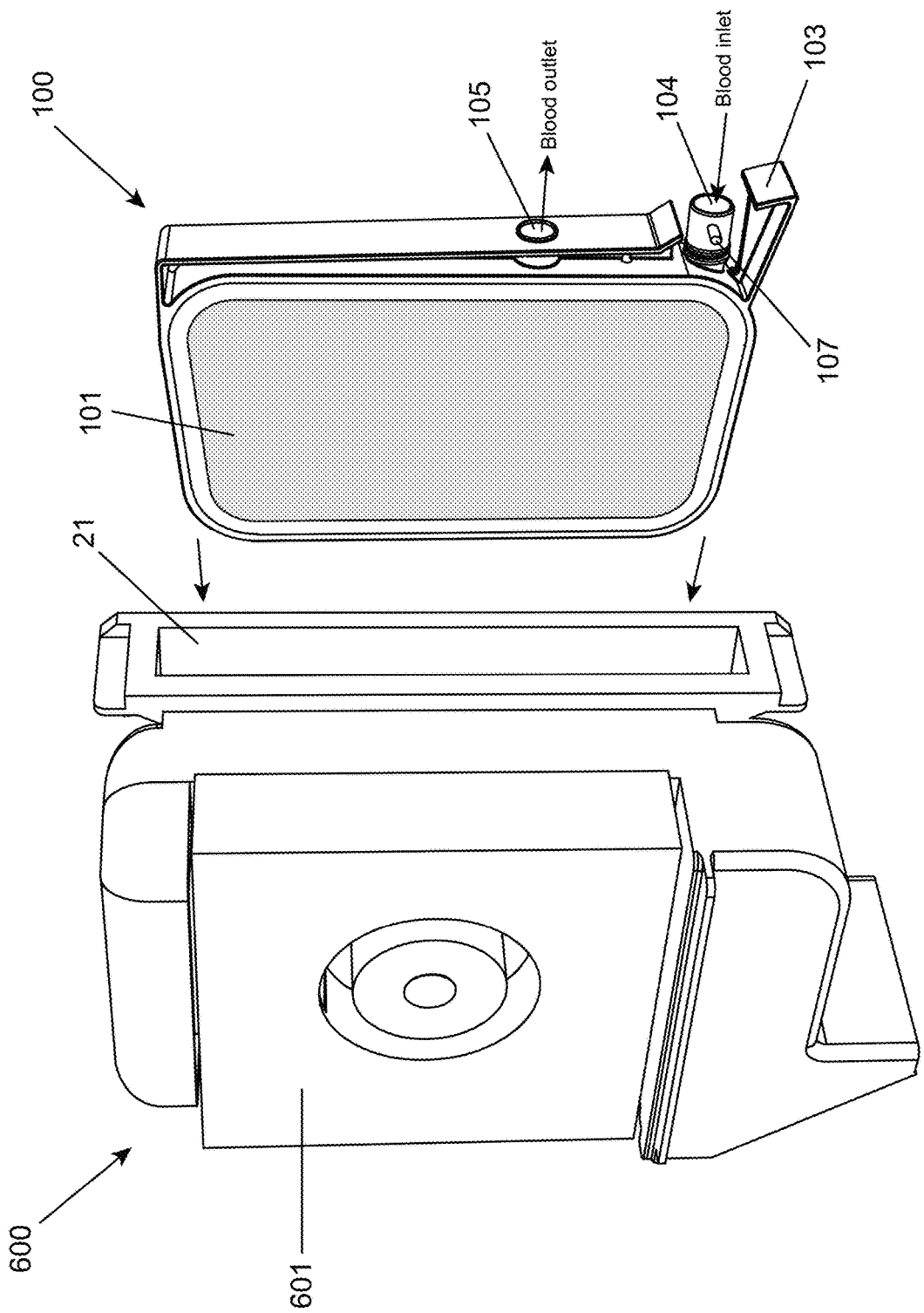
FIG. 5 is a view of the heater/cooler unit 600, contained within the transportable machine body 2, and of the heat exchanger 100.

A slot 21, here having a vertical orientation, is formed on the front part of the machine body, for receiving a heat exchanger 100 (see also FIG. 5).

Referring in particular to FIG. 5, the heat exchanger 100 has a flat shape. The blood enters the heat exchanger 100 through the inlet port 104 and as it flows from the bottom to the top, it enters in contact with the metal plate 101 that is heated or cooled by the heater/cooler unit 600, providing for a thermoregulation of the blood. Once the blood has reached the top of the heat exchanger and has been thermoregulated, it exits from outlet port 105 passing through an internal channel of the heat exchanger.

Figure 2:
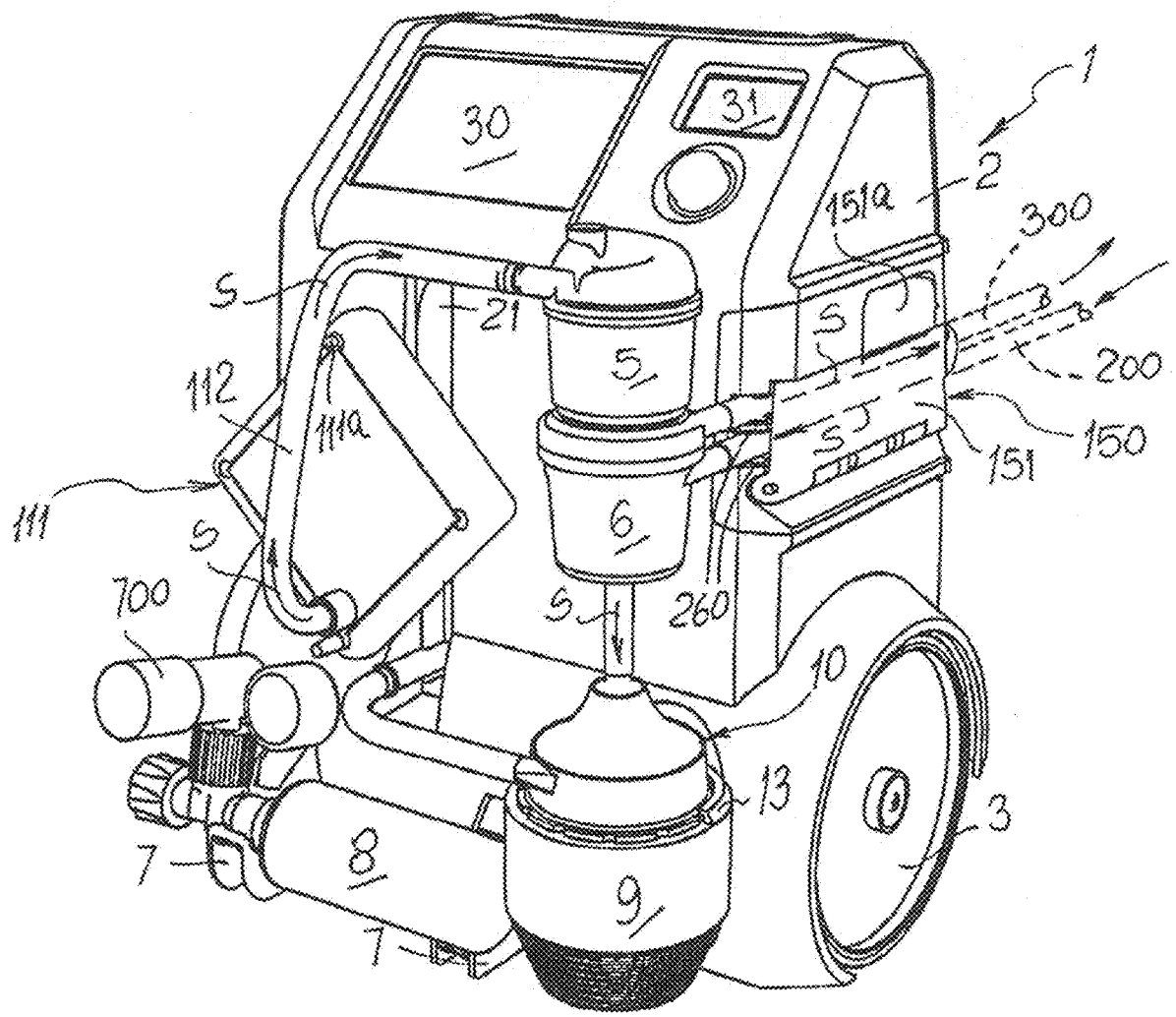
FIG. 2 is a perspective view of the medical apparatus of FIG. 1, as taken under a different angle of view.

Referring now to FIGS. 1 and 2, the machine body 2 has a pair of supports 7 in its lower front portion, preferably just below the slot 21, which supports are designed to receive and hold at least one bottle 8 containing a gas adapted to be administered to the patient "P" under therapy, which is typically oxygen.

Still in the lower front part, the machine body 2 also supports a motor unit, which is held in a housing 9 integrated with the machine body 2 and has connection members in its upper portion, e.g. a bayonet connection 13, for coupling with a pump 10 that receives motion from the motor and is designed to circulate blood in the extracorporeal circuit 500.

Two display screens 30 and 31 are provided in the upper portion of the machine body 2, which are adapted to display the physiological data of the patient "P" and the components of the extracorporeal circuit 500 are controlled and monitored by touch screen controls.

Still in the front part, the machine body 2 supports a filtering unit for filtering the blood of the patient "P", namely an arterial filter 5 and a venous filter 6, which are mounted one above the other and have elements for removing any air in the blood of the patient "P".

The venous filter 6 receives a line 200 for drawing venous blood from the patient "P" and a return line 300 extends from the arterial filter 5 for returning the arterial blood to the patient "P" after treatment by the medical apparatus 1.

The oxygenator 111 and the arterial filter 5 are connected together by a connection line 112, whereas the pump 10 is connected with the exchanger 100 by a connection line 109.

The term "connection line" is intended to designate a tube for the flow of blood of the patient "P" or a liquid medical solution.

Referring to FIG. 1, the machine body 2 has an opening 22 on one side, which is protected by a grid and is used to draw cooling air from the outside by means of the fan 601 (FIG. 5).

On the opposite side, as shown in FIG. 2, the machine body 2 has a detection station 150 in which both the venous line 200 and the arterial line 300 extend, and in which the parameters of the inflowing and outflowing blood of the patient "P" are detected during treatment.

The detection station 150 comprises a housing which receives respective segments of the two venous 200 and arterial 300 lines, which housing is protected by a cover 151 adapted to be opened for access to the housing when needed, by pressing a button 151a.

Figure 3:
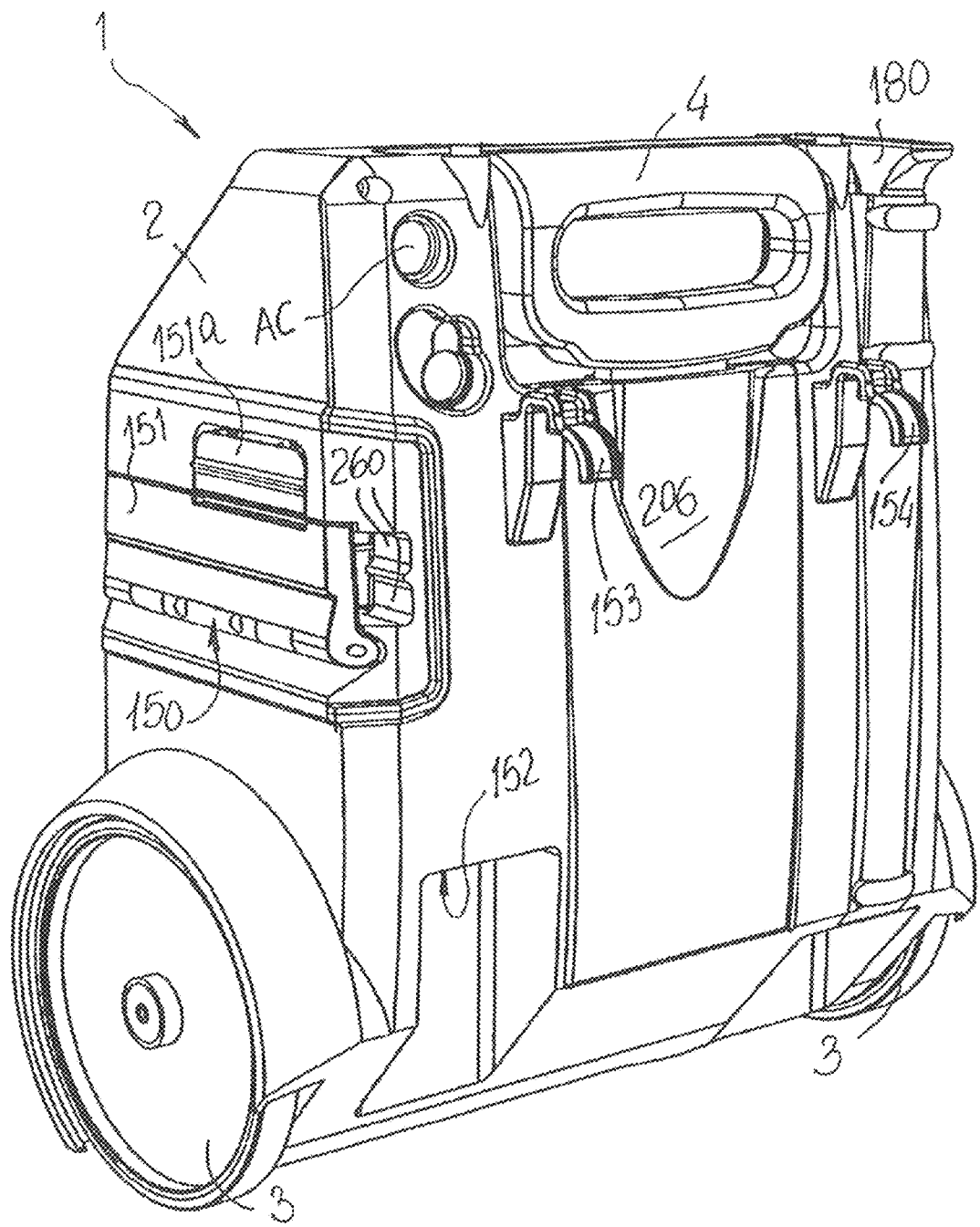
FIG. 3 is a rear view of the medical apparatus of FIG. 1.

Referring to FIG. 3, an outlet 152 is formed in the lower portion of the back of the apparatus 1, for evacuation of any air that enters through a lateral opening 22.

Still on the back of the machine body 2 two hooks 153 and 154 are provided for coupling, when needed, the medical apparatus 1 to the bed of a patient after his/her hospitalization in a hospital facility, without having to disconnect it from the extracorporeal circuit 500; numeral 180 designates an extractable rod having a hook at its top which rod, in its upwardly extracted position, is designed to support bags 501 containing liquid medical solutions to be infused to the patient "P".

In the Figures, the arrows "S" designate the flow direction of the blood of the patient "P" along the extracorporeal circuit 500.

Figure 4:
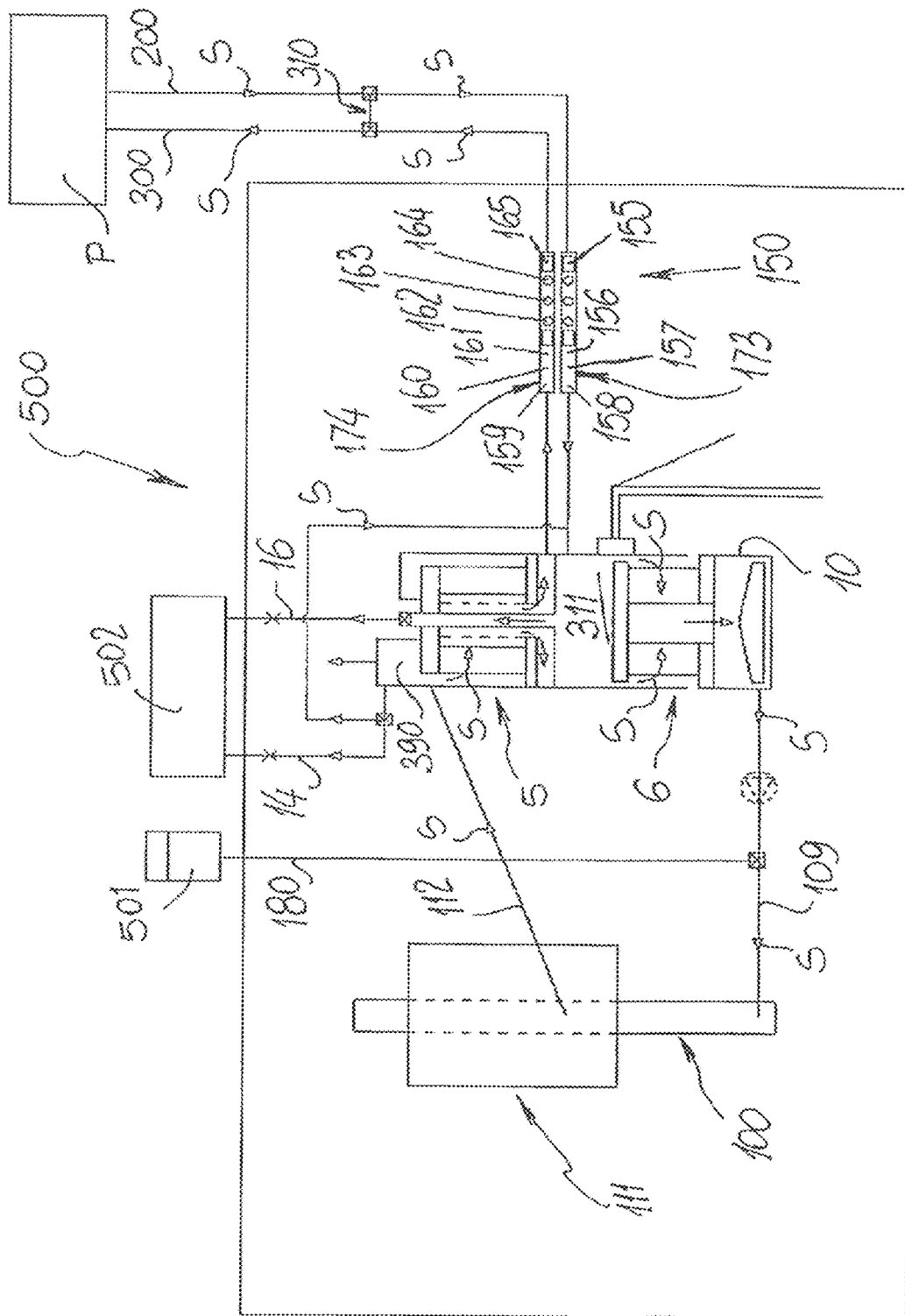
FIG. 4 is a diagrammatic block view of the extracorporeal circuit of the medical apparatus of FIG. 1.

Referring to FIG. 4, the rectangle 2 schematically designates the machine body of the medical apparatus 1 with all the elements that form the extracorporeal circuit 500 integrated thereto.

The term "integrated" is intended to mean that the elements are mounted or fixed to the machine body 2 and do not float in the surrounding space.

Only the two venous drawing 200 and arterial return 300 lines extend outside the machine body 2 of the medical apparatus 1 to reach the points of connection with the vessels of the cardiovascular system of the patient "P".

It shall be noted that the two venous 6 and arterial 5 filters both have chambers for collecting any air in the blood, which are designated by numerals 311 and 390 respectively.

Both may in turn be connected by respective connection lines 14 and 16 to a collecting reservoir 502, which is adapted to be removably placed on the machine body 2 and may consist, for instance, of a syringe having an adequate capacity to contain air and residues collected by the filter elements 5 and 6.

As shown in the Figures, both venous 200 and arterial 300 lines extend through the detection station 150, where two elements 173 and 174 are arranged, each with one of the lines extending therethrough (see FIG. 4 in detail).

The two elements 173 and 174 may be two solid housing bodies, which are supported in the compartment of the detection station 150 by guide segments 260 and where housing seats are formed for a plurality of detection sensors, adapted to detect certain critical parameters of the blood of patients "P", while blood flows towards or away from the extracorporeal circuit 500 and display them on the two display screens 30 and 31.

For instance, the element 173 with the venous line 200 extending therethrough may accommodate a venous pressure sensor 155 at its inlet, in the direction "S" and a blood temperature sensor 156 downstream therefrom, which is in turn followed by a hematocrit and/or hemoglobin sensor 157 and an oxygen saturation sensor 158.

The element 174 may be equipped at its inlet with an arterial blood flow measuring sensor 159 which is successively followed by an air micro-bubble sensor 160, an arterial blood temperature sensor 161, a pH sensor 162, a carbon dioxide pressure sensor 163, an oxygen pressure sensor 164 and an arterial pressure sensor 165.

All the detected values may be displayed and recalled by medical and health care personnel on the display screens 30 and 31.

Referring to FIG. 5, numeral 600 represents a thermoelectric heater/cooler unit entirely contained within the transportable machine body 2, while numeral 21 is a slot within the heater/cooler unit 600 for receiving the heat exchanger 100.

Figure 6:
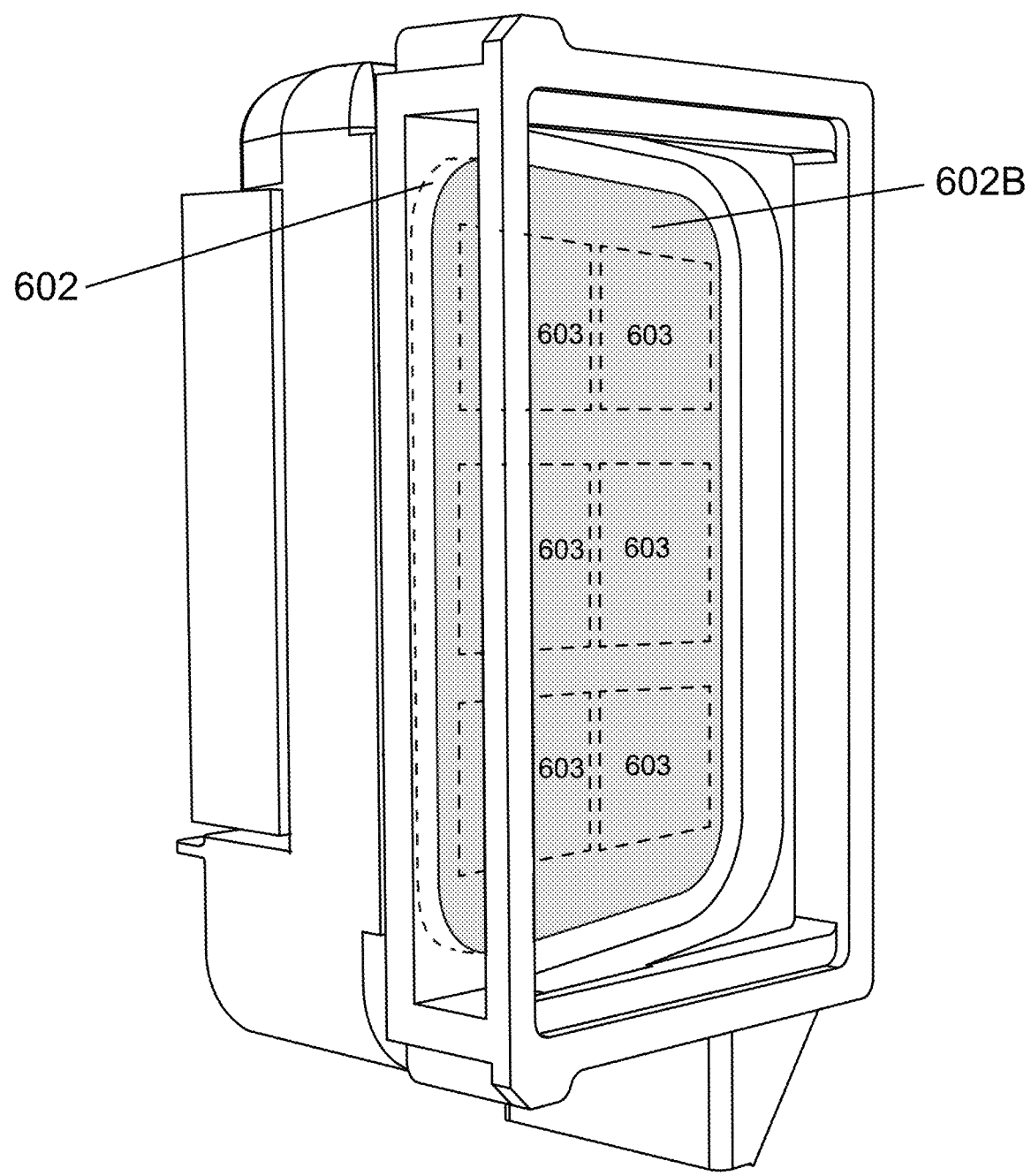
FIG. 6 is a view of the heater/cooler unit 600, taken under a different angle of view.

The heater/cooler unit 600 can generate heat or can cool due to a series of Peltier cells 603 integrated inside the unit itself (see also FIG. 6).

The heater/cooler unit 600 works without requiring any fluids, whether in liquid or gas form.

Figure 8B:
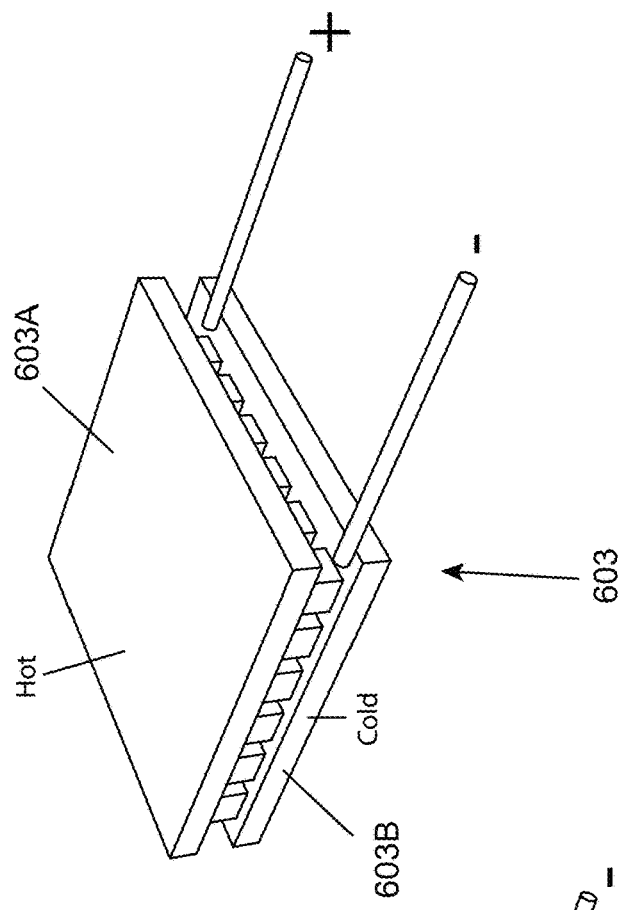
FIG. 8A and 8B are perspective views of a Peltier cell.
Figure 8A:
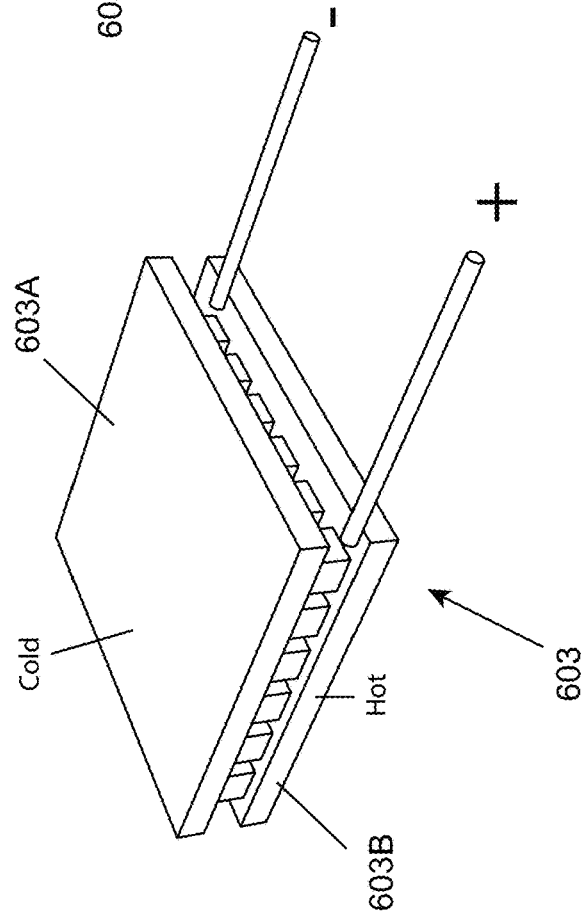

Peltier cells (the operating principle of which is the Peltier effect) can be used either for heating or for cooling depending on the direction of the current that flows through them (therefore, on the polarity of the applied voltage). Referring to FIG. 8A, with a given polarity of the applied voltage, the element 603A of the Peltier cell 603 becomes cold and the element 603B becomes hot; by applying the opposite polarity (FIG. 8B) the element 603A becomes hot and the element 603B becomes cold.

Figure 7:
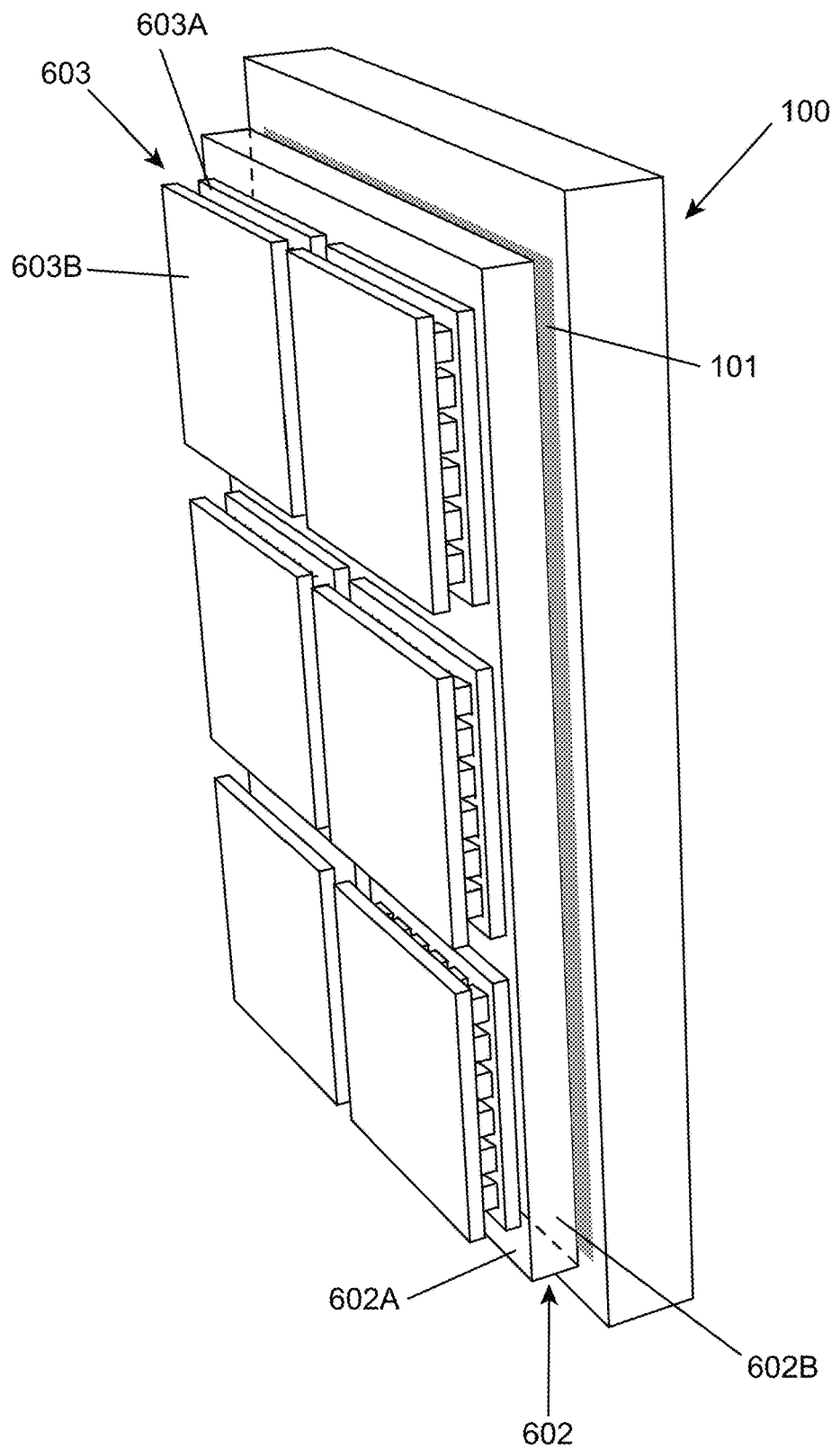
FIG. 7 is a schematic representation of metal plates 602, heat exchanger 100 and Peltier cells 603.

Referring to FIGS. 6 and 7, Peltier cells 603 are fixed to a metal plate 602 so that the elements 603A of the cells are in strict contact with face 602A of the metal plate itself.

When the heat exchanger 100 is inserted in the slot 21 (see also FIG. 5), its metal plate 101 comes into strict contact with the face 602B of metal plate 602.

When the blood must be warmed up, the voltage applied to the Peltier cells is such that the cell elements 603A in contact with the metal plate 602 become hot; the heat is transferred from the Peltier cells to the metal plate 602 and consequently to the metal plate 101, which in turn transfers the heat to the blood that flows inside the heat exchanger 100.

On the contrary, when the voltage applied to the Peltier cells is such that the cell elements 603A in contact with the metal plate 602 become cold, the blood is cooled down.

Referring to FIG. 5, numeral 103 designates an elastic hook engaging an inner edge of the slot 21 when the heat exchanger 100 is introduced into the slot 21, to prevent it from accidentally coming out of it, whereas numeral 104 designates a connection mouth to connect the line 9 that extends from the pump 10, through which the blood enters in the heat exchanger, and numeral 105 designates the outlet port for the blood, to be connected to the oxygenator inlet port.

A connector 107, typically a Luer connector is provided on the connection line, for filling the extracorporeal circuit with a washing solution or a biological solution before use, which is known as "priming".

It shall be remembered that, in addition to a conventional cable for connection to the mains and an "AC" power switch button on the back, the medical apparatus 1 has a standalone power supply unit, not shown, e.g. one or more rechargeable accumulators, which allow standalone operation even when no connection to the power mains is available.

Operation

Operation of a medical apparatus 1 according to the invention is as follows:

when a health care operator performs a rescue intervention on a patient struck a serious disease, he/she will carry the transportable medical apparatus 1 with him/her, e.g. by loading it on a rescue vehicle or manually dragging it after extracting the handle 4 from the compartment.

Initially, the operator mounts all the disposable components to the machine body 2 to perform the therapy required by the rescue intervention, and particularly the heat exchanger 100 is inserted into the slot 21.

The venous 6 and arterial 5 filters are also mounted, after being connected to the venous drawing 200 and arterial return 300 lines, which lines are temporarily short-circuited for the necessary priming step and are also connected to the pump 10, whereupon the oxygen bottle 8 is eventually placed on the supports 7, by connecting the pressure reducer 700 when needed, with the mouth 111a.

Then the various components and their connection lines, e.g. 109 and 112 are connected together, and the medical apparatus 1 is ready for use.

When the health care operator reaches the patient that has been struck by the disease, he/she will connect the drawing or venous line 200 and the return or arterial line 300 to respective vessels of the patient and, before starting the patient's blood flow and initiating the rescue therapy, he/she will temporarily connect together the two venous 200 and arterial 300 lines, by opening a bypass 310 and perform a quick filling or priming step for filling the extracorporeal circuit 500 with a blood compatible solution, e.g. a saline, by introducing it through the connector 107 to fill the extracorporeal circuit and reduce the blood volume to be withdrawn from the patient "P".

Once the priming step has been completed, the operator will close the bypass 310 and start withdrawing blood from the patient, which blood flows in the drawing line 200 through the detection station 150, namely through the element 173.

As blood flows through this element 173, the physical and blood parameters of the venous blood withdrawn from the patient "P" are detected, such as venous pressure by the sensor 155, temperature by the sensor 156, hematocrit and/or hemoglobin by the sensor 157 and oxygen saturation by the sensor 158.

All these sensors are typically mounted in their seats within the element 173, which is situated in the detection station 150.

The detected parameters are transmitted to a controller (not shown), which controls the operation of the medical apparatus 1, and are further transmitted by the controller to the display screens 30 and 31, to e displayed by health care operators.

Therefore, blood enters the venous filter 6, in which it is cleared of any air it may contain and is pushed inside the heat exchanger 100 by the action of the pump 100 via the connection line 109.

Once blood has been thermally treated in the heat exchanger 100, it flows into the oxygenator 111 and is transmitted therefrom, via the connection line 112, to the arterial filter 5, in which it is further filtered for removing any residual air micro-bubbles.

Then, blood is pushed from the arterial filter 5 through the element 174 in the detection station 150 before being conveyed back to the patient "P" via the arterial line 300.

As blood flows through this element 174, further blood parameters are detected, which are also displayed on the display screen of the medical apparatus 1, and namely the detected parameters may include flow rate detected by the sensor 159, residual micro-bubbles, detected by the sensor 160, temperature detected by the sensor 161, pH detected by the sensor 162, carbon dioxide pressure detected by the sensor 163, oxygen pressure detected by the sensor 164 and arterial pressure detected by the sensor 165.

If needed, as the operator performs adequate rescue therapies on the patient "P", he/she can also administer the gas, e.g. oxygen, contained in the bottle 8, by connecting it to the mouth 111a and preparing it for direct administration if no alternative oxygen supply source can be used.

The provision of two display screens 30 and 31 also allows the parameters detected in the detection station 150 to be displayed on one of them only, whereas the other provides the touch screen buttons for actuating and controlling the operation of the medical apparatus 1, or allows use of one of these display screens when the other is out of service.

After a first rescue intervention, the patient "P" may be sent to a hospitalization facility, i.e. a clinic or a hospital, while still being connected to the medical apparatus 1 which, after hospitalization, may keep on operating, as it can be coupled to the bed of a hospitalized patient "P", using the hooks 153 and 154.

At the end of the operation of the medical apparatus 1, all disposable components in the machine body 2 are removed, with the body being ready to receive replacing parts whenever the apparatus is required to be used again.

The invention has been found to fulfill the intended objects.

The invention so conceived is susceptible to changes and variants within the inventive concept.

Also, all the details may be replaced by other technical equivalent elements.

In practice, any material, shape and size may be used as needed, without departure from the scope as defined by the following claims.

The invention claimed is:

1. A portable medical apparatus for cardiopulmonary aid to patients comprising:
   a transportable machine-body having a housing, at least one coupling seat being defined in the housing and configured for removable coupling with a heat exchanger; and
   an extracorporeal circuit for a patient's blood circulation, said heat exchanger thermo-regulating the patient's blood in said extracorporeal circuit,
   wherein said housing houses a heater/cooler unit, working without use of a fluid, for thermoregulating the patient's blood inside said heat exchanger,
   wherein said extracorporeal circuit comprises,
      a venous blood drawing-line from said patient and an arterial blood return-line to said patient,
      a pumping unit for pumping blood along the extracorporeal circuit, and
      an oxygenator unit for oxygenating the blood,
   wherein said heater/cooler unit is entirely contained within the housing,
   wherein said coupling seat is defined as a slot within said heater/cooler unit for receiving said heat exchanger, and
   wherein said heat exchanger has a flat shape, configured to enable introduction into said slot.

2. The portable medical apparatus according to claim 1, wherein said extracorporeal circuit comprises an arterial filter.

3. The portable medical apparatus according to claim 1, wherein said extracorporeal circuit comprises a venous filter.

4. The portable medical apparatus according to claim 1, wherein said machine-body comprises at least a couple of wheels arranged at a lower end of said machine-body.

5. The portable medical apparatus according to claim 1, wherein said machine-body comprises an extractable handle for lifting and dragging the portable medical apparatus.

6. The portable medical apparatus according to claim 1, wherein said machine-body comprises a check-up station to check-up physical and hemo-chemical parameters of the patient's blood flowing in said extracorporeal circuit.

7. The portable medical apparatus according to claim 6, wherein said check-up station comprises at least two housing elements of sensing devices of said physical and hemo-chemical parameters, a first housing element being placed on or passed through by said drawing line, and a second housing element being placed on or passed through by said return line.

8. The portable medical apparatus according to claim 6, wherein said machine-body comprises at least a first display screen, on which one or more of hemo-chemical or physical parameters of the patient's blood, checked-up in said check-up station, are displayed.

9. The portable medical apparatus according to claim 8, wherein said machine-body comprises a second display screen, which is alternated to or associated to said first display screen.

10. The portable medical apparatus according to claim 1, wherein said pumping unit comprises a motor unit.

11. The portable medical apparatus according to claim 1, wherein said machine-body comprises a support for a container of a gas to be administered to said oxygenator unit, said support being integral with an outwardly facing portion of said machine-body.

12. The portable medical apparatus according to claim 1, wherein said machine-body further comprises an extractable holder for holding a container of a liquid medical solution to be transfused to said patient at a high position with respect to said machine-body.

13. The portable medical apparatus according to claim 1, wherein said oxygenator unit is removably coupled to said heat exchanger.

* * * * *